(12) United States Patent
Schleuning

(10) Patent No.: US 8,557,287 B2
(45) Date of Patent: Oct. 15, 2013

(54) SILICONE GEL COMPOSITION AND DISPENSER THEREFOR

(76) Inventor: Jeff S. Schleuning, Las Vegas, NV (US)

( * ) Notice: Subject to any disclaimer, the term of this patent is extended or adjusted under 35 U.S.C. 154(b) by 1674 days.

(21) Appl. No.: 10/913,656

(22) Filed: Aug. 6, 2004

(65) Prior Publication Data

US 2006/0029672 A1    Feb. 9, 2006

(51) Int. Cl.
*A61K 9/14*    (2006.01)
(52) U.S. Cl.
USPC .......................................................... 424/484
(58) Field of Classification Search
USPC .......................................................... 424/484
See application file for complete search history.

(56) References Cited

U.S. PATENT DOCUMENTS

2002/0028223 A1 *    3/2002   Vatter et al. ................... 424/401

* cited by examiner

*Primary Examiner* — Blessing M Fubara
(74) *Attorney, Agent, or Firm* — Snell & Wilmer L.L.P.

(57) ABSTRACT

A therapeutic silicone composition and a delivery device operable for the self-administration of the therapeutic silicone composition to the skin. Silicone gel compositions are known in the art to promote wound healing and reduce scarring. The therapeutic silicone composition of the present invention contains a silicone gel formulated with inert thickening agents and/or carriers sufficient to provide a firm, semi-solid silicone gel material that substantially retains its shape when extruded from a tube. When topically applied to hypertrophic tissue, the composition, which is applied as a light film to cover the tissue, is transparent and substantially dry, obviating the need for an occlusive dressing.

2 Claims, 1 Drawing Sheet

SILICONE GEL COMPOSITION AND DISPENSER THEREFOR

BACKGROUND OF THE INVENTION

1. Field of the Invention

The present invention relates to a therapeutic silicone gel composition formulated for topical application for the treatment of hypertrophic conditions of the skin such as keloids.

2. Prior Art

Keloid and hypertrophic scars appear on the skin after injury or acne which usually causes much distress, both aesthetic and functional, to the patient and can become a lifelong problem unless medically treated. Silicone gel or a gel-coated occlusive sheeting is widely used for the treatment of hypertrophic and keloid scars, though at present there is no scientific explanation as to its mode of action. With silicone gel treatment, softening and flattening of scars is observed after months of continuously covering of the scar with a layer of the silicone gel.

The skin and the dermis of hypertrophic and keloid scars are histologically and chemically different from that of intact skin. In the epidermis of these scars the keratin layer is thin or even absent, while in intact skin, keratin forms an insulating layer. Due to the extended period of time required to produce a therapeutic result, it is an object of the present invention to provide a "dry" silicone gel composition that can be applied directly to the effected skin without the need for an occlusive dressing; the composition being operable for the non-invasive treatment of hypertrophic and keloid scars. There is a further need for a dispenser for the "dry" therapeutic silicone gel composition which renders the composition easy to self-administer.

There have been many prior art attempts to provide a wound covering that reduces excessive scarring during the healing process. U.S. Pat. No. 4,725,279 discloses a biocompatible material for a thermal burn dressing. The material is a composite comprising a thin film of thermoplastic material such as Silastic. U.S. Pat. No. 4,838,253 discloses a liquid permeable dressing comprising one or more sheets of apertured material, such as cotton gauze, coated with a tacky silicone gel or a non-tacky silicone elastomer. U.S. Pat. No. 5,395,305 discloses a wound-covering material comprising two layers: a first support layer which is in contact with the wound and which contains a water-repellant substance and a second moisture permeation controlling layer which may be formed from permeable resin films made of silicone or polyurethane elastomers. U.S. Pat. No. 5,196,190 discloses a membrane suitable for wound dressing comprising a natural or synthetic polymer, a non-gellable polysaccharide and a cross-linking agent. U.S. Pat. No. 3,803,300 discloses an ointment foil for application to skin. The ointment foil is prepared by drying an oil-in-water emulsion of ointment ingredients to a moisture content of 1% to 15%. U.S. Pat. No. 3,867,520 discloses a medicated polyamino acid film for occlusive dressing therapy.

Notwithstanding the advances made in prior art wound dressings for the reduction of scar formation, there remains a need for compositions and devices for administering the compositions which are operable for reducing the profile of a scar after the wound has healed and the scar has already formed. Silicone gel is known to reduce the profile of scars but in accordance with the prior art, silicone gel is held in contact with the scar by an occlusive dressing which is unsightly and inconvenient to use. Accordingly, there is an ongoing need for a silicone gel composition operable for the non-invasive treatment of hypertrophic and keloid scars and a dispenser for the therapeutic silicone gel composition which renders the composition easy to self-administer.

SUMMARY

The present invention is directed to a therapeutic silicone gel composition and a device for administering the composition that substantially obviates one or more of the limitations of the prior art. To achieve these and other advantages and in accordance with the object of the invention as broadly described herein, the invention includes a relatively dry silicone gel composition operable for the non-invasive treatment of hypertrophic and keloid scars.

It is a further object of the invention to provide a dispenser operable for administering a therapeutic silicone gel composition meeting the above objective which renders the therapeutic silicone gel composition easy to self-administer.

The features of the invention believed to be novel are set forth with particularity in the appended claims. However the invention itself, both as to organization and method of operation, together with further objects and advantages thereof may be best understood by reference to the following description taken in conjunction with the accompanying drawings.

DESCRIPTION OF THE PREFERRED EMBODIMENTS

A preferred therapeutic silicone composition in accordance with the present invention is a firm, semisolid (at room temperature), homogeneous mixture comprising polydimethylsilicone, candelilla wax, Vitamin E, cetyl dimethicone copolyol, and Bisabolol.

Example 1

85 Grams of silicone gel comprising 60 Grams of cetyl dimethicone copolyol and 25 grams polydimethylsilicone is added to 8 grams of melted candelilla wax containing 8 grams of cera alba and the melt is stirred. 0.5 grams of Vitamin E, 0.4 grams of bisabolol and 0.02 grams of EDTA is added to the solution with continued stirring and 5 ml aliquots of the resultant solution are transferred to the reservoir 14 (see FIG. 1) of a dispenser and cooled to room temperature. Upon cooling, the resultant silicone gel composition is firm and substantially retains its structural integrity when extruded from the reservoir of the dispenser as, for example, with a lipstick, and may be applied to the skin to form a thin layer of the therapeutic silicone gel composition thereon.

Figure 1:
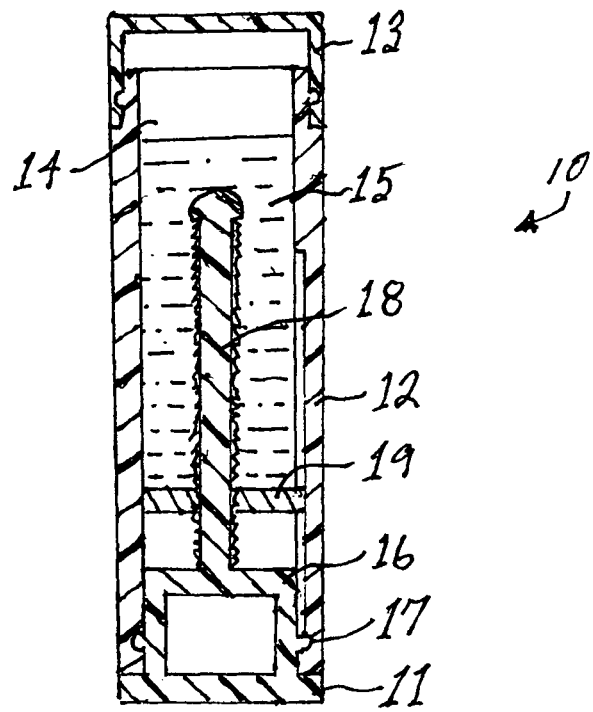
FIG. 1 is a longitudinal cross-sectional view of a silicone gel dispenser in accordance with a "twist-to-extrude" embodiment of the present invention.
Figure 2:
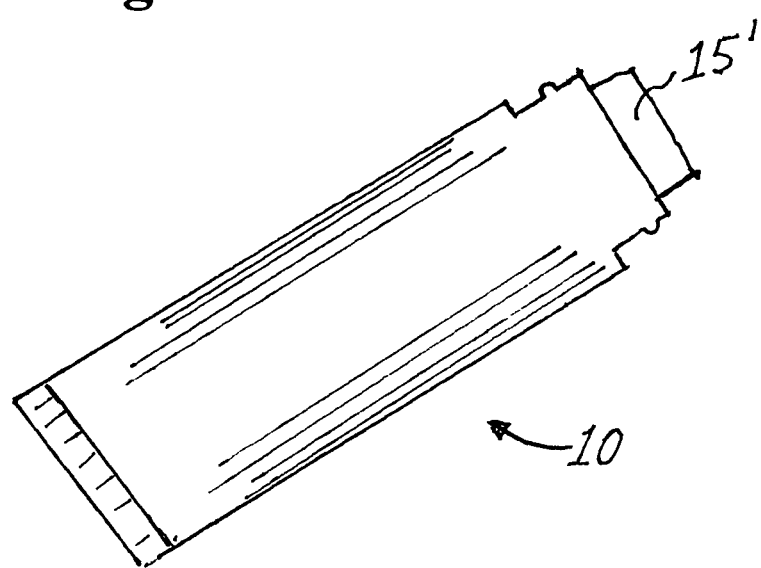
FIG. 2 is a perspective view of a silicone gel dispenser in accordance with FIG. 1 showing an exposed portion of the composition extruded from the dispenser in preparation for application to a scar.

FIG. 1 is a longitudinal cross-sectional view of a silicone gel dispenser 10 in accordance with a "twist-to-extrude" embodiment of the present invention. The dispenser 10 comprises a base 11, a body portion 12 and a cap 13. The body portion 12 has a cylindrical inner chamber 14 that serves as a reservoir for containing the composition 15. The base 11, which is rotatably attached to the body portion 12 by means of an annular ridge 16 that matingly engages an annular groove 17 in the inner wall of the reservoir 14, has a threaded elongate member 18 integral therewith. A disc-shaped nut 19 provides a movable plunger that is advanced or retracted within the chamber by twisting the base 11. The base, body portion and cap are preferably made from a rigid elastomer such as polyethylene. FIG. 2 is a perspective view of the silicone gel dispenser 10 in accordance with FIG. 1 with the cap 13 removed showing an exposed portion 15' of the composition extruded from the dispenser in preparation for application to a scar.

While a particular embodiment of the present invention has been illustrated and described, it would be obvious to those skilled in the art that various other changes and modifications can be made without departing from the spirit and scope of the invention. For example, the percentage of the components in the silicone gel-wax composition may be varied to suit the intended application. The relative concentrations of components presented herein are exemplary and not intended to limit the scope of the invention. Similarly, the dispenser 10 may comprise an open-ended syringe wherein depression of the plunger extrudes composition from the barrel for application to the skin. It is therefore intended to cover in the appended claims all such changes and modifications that are within the scope of this invention.

What I claim is:

1. A process of making a firm, semi-solid silicone composition comprising the steps of:
    a. melting 7.85 wt. % of candelilla wax with 7.85 wt. % cera alba to form a molten mixture;
    b. mixing 58.87 wt. % cetyl dimethicone copolyol with 24.53 wt. % polydimethylsilicone to form a silicone gel;
    c. adding said silicone gel into said molten mixture with stirring;
    d. adding 0.49 wt. % of Vitamin E, 0.39 wt. % of bisabolol, and 0.02 wt. % EDTA into said molten mixture with continued stirring; and
    e. transferring said molten mixture in aliquots to a reservoir of a dispenser and allowing said molten mixture to cool to room temperature, wherein said composition is firm at room temperature and substantially retains its shape when extruded from said dispenser.

2. A method for treating hypertrophic tissue of the skin comprising the topical application of a silicone gel composition made in accordance with the process of claim 1 directly to the hypertrophic tissue.

* * * * *